United States Patent [19]

Ryan

[11] 4,275,444
[45] Jun. 23, 1981

[54] ARRANGEMENTS FOR CONSTRUCTING REPRESENTATIONS OF PARTS OF BODIES

[75] Inventor: John L. Ryan, Chalfont St. Peter, England

[73] Assignee: EMI Limited, Hayes, England

[21] Appl. No.: 37,919

[22] Filed: May 9, 1979

[30] Foreign Application Priority Data

May 12, 1978 [GB] United Kingdom ............... 19148/78

[51] Int. Cl.$^3$ ............................................. G06F 15/42
[52] U.S. Cl. ............................... 364/414; 250/445 T; 364/515
[58] Field of Search .............................. 364/414, 515; 250/445 T, 363 S; 358/111

[56] References Cited

U.S. PATENT DOCUMENTS

| | | | |
|---|---|---|---|
| 3,778,614 | 12/1973 | Hounsfield | 250/362 |
| 3,924,129 | 12/1975 | LeMay | 250/336 |
| 4,002,910 | 1/1977 | LeMay | 250/445 T |
| 4,010,371 | 3/1977 | LeMay | 250/445 T |
| 4,035,647 | 7/1977 | Hounsfield | 250/445 T |
| 4,044,240 | 8/1977 | Cox, Jr. et al. | 250/445 T |
| 4,075,483 | 2/1978 | Tancrell et al. | 250/363 S |
| 4,138,611 | 2/1979 | Hounsfield | 250/445 T |
| 4,144,570 | 3/1979 | Wagner | 364/414 |
| 4,149,250 | 4/1979 | Jass | 250/445 T |
| 4,168,435 | 9/1979 | Duinker | 250/445 T |

FOREIGN PATENT DOCUMENTS 2521796  11/1976  Fed. Rep. of Germany ........... 364/414

OTHER PUBLICATIONS

Herman et al., "Reconstruction Using Divergent-Ray Shadowgraphs"; *Reconstruction Tomography in Diagnostic Radiology and Nuclear Medicine;* ed. Ter Pogossian et al., pp. 105-117.

*Primary Examiner*—Errol A. Krass
*Attorney, Agent, or Firm*—Cooper, Dunham, Clark, Griffin & Moran

[57] ABSTRACT

In CT scanners signals representing attenuation of radiation along beam paths through the patient may be processed by a convolution technique to give radiation absorption values for a matrix of elements in a region of interest. It the beams are distributed in a fan-shape from a focus the convolution can be applied but the signals need to be weighted by a factor related to the distance of a respective matrix element from the focus. By consideration of the geometry of a CT scanner of this kind it has been found that the weighting may be achieved more efficiently if the signals for all beams are pre-weighted by a factor related to the angular position of the beam in the fan, leaving only a simple scaling factor which needs to be applied for each martrix element.

8 Claims, 7 Drawing Figures

ARRANGEMENTS FOR CONSTRUCTING REPRESENTATIONS OF PARTS OF BODIES

The present invention relates to the processing of signals representing measurements of a quantity in a region of interest, to construct a representation of the distribution of the quantity in the region. It is particularly related to the processing of measurements of attenuation of penetrating radiation, in a slice of a patient, to derive a representation of the distribution of attenuation of the radiation with position in the slice.

In U.S. Pat. No. 3,778,614 there is described apparatus known as computerized tomographic (CT) apparatus, for obtaining and processing such measurements of attenuation. The apparatus includes a source of penetrating radiation and detector means responsive to the radiation. The source and detector means are scanned, in the slice and relative to the body, so that the detector means provides output signals which, after pre-processing steps, can be processed to give the desired representation. The said United States patent describes a suitable method for processing the signals. An improved form of that processing, which is based on convolution, is described in U.S. Pat. No. 3,924,129. As described in both Patent Specifications the detector output signals are organised into sets, each of which can conveniently comprise attenuation values, relating to corresponding paths of a set of paths of the radiation through the slice being examined. Each set is then operated upon so that each signal is modified by combination with contributions from other signals. The modified signals are "mapped" into storage locations corresponding to elements of a matrix of elements notionally defined in the slice. The distribution is such that each location holds the sum of all modified signals for radiation paths the centre lines of which pass through the corresponding element in the slice. To ensure that the distribution to each storage location is related to the extent of interception of the element in the region of interest by the beam paths, the modified signals are interpolated to provide a larger number of signals corresponding to attenuation of radiation in respective ones of an increased number of radiation paths.

Although the sets of detector output signals can conveniently correspond to sets of parallel paths, this is not necessary. In some forms of CT apparatus, described for example in U.S. Pat. No. 4,035,647, examination is by sets of radiation beams distributed in a fan originating at the radiation source. It is then convenient to process the signals for fan distribution of paths corresponding to different positions of that fan of beams. This can be achieved using the said processing but, if the embodiment of the processing based on convolution is employed, consequential additional modifications are required as the modified signals are distributed to the corresponding storage locations. Suitable modifications for the convolution method have been described in U.S. Pat. No. 4,010,371 and the theory of such modifications has been described by Herman, Lakshminarayanan and Naparstek "Reconstruction using Divergent-Ray shadowgraphs" from "Reconstruction Tomography in Diagnostic Radiology and Nuclear Medicine" ed. Ter. Pogossian et. al pp. 105–117, 1977, University Park Press Baltimore U.S.A. and others. The distribution of the additionally modified signals to the required storage locations can be achieved without undue difficulty but the stages to be followed are relatively inefficient in organisation of the paths which the signals follow through the processing and can result in long processing times. It is an object of this invention to provide a method of achieving the distribution which is more efficient.

According to the invention there is provided an apparatus for processing signals, each of which represents the attenuation of radiation along individual beam paths of a corresponding one of a plurality of fan-shaped distributions of beam paths directed through the body of a patient to provide a representation of the distribution of attenuation of the radiation in a slice of said body, the apparatus including: means for modifying the signals by combination with weighted contributions from other signals of the same set; means for distributing from each set, to each of a plurality of storage locations representing elements of a matrix of elements notionally defined in said slice, one modified signal, relating to a path which intersects that element or a value interpolated between the signals to relate to a notional path intersecting the element; and means for effectively weighting each signal distributed to an element by a weighting factor inversely proportional to a power of the distance D of the respective element from the focus of the distribution of beam paths to which the signal is related; wherein the means for effectively weighting includes means for multiplying each of the modified and interpolated signals of a set by a power of Cos $\theta$, where $\theta$ is the angle of the respective path to the perpendicular to a plurality of parallel lines of matrix elements and scaling means for weighting all signals to be distributed to matrix elements on one of said lines by a scaling factor chosen for the respective line to complete the required weighting.

In order that the invention may be clearly understood and readily carried into effect, it will now be described by way of example, with reference to the accompanying drawings, of which.

Figure 1:
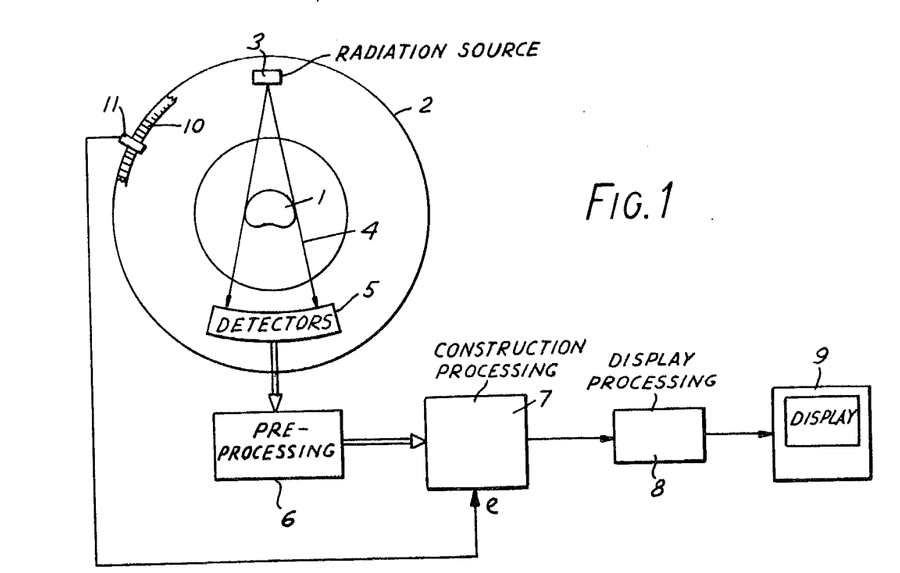
FIG. 1 illustrates in simplified form a CT apparatus embodying the invention.

FIG. 1 shows in diagrammatic form a CT apparatus embodying this invention. Output signals, relating to the attenuation of radiation in a body 1, are obtained in a scanning apparatus indicated generally at 2. This scanning part, which includes source 3, directing a fan distribution of radiation 4 through body 1, and detectors 5, receiving the radiation, is illustrated as the type described in U.S. Pat. No. 4,035,647 which is hereby incorporated by reference in this application. It can, however take other suitable forms known for CT apparatus, for example that described in U.S. patent application Ser. No. 772,689 filed in Feb. 28, 1977, in the name of Colin C. Oliver and assigned to EMI Limited. The output signals are preprocessed by circuits 6, in which they are, for example, converted to logarithmic and digital form, to take the form of measurements of attenuation of the radiation for the paths along which it has passed through the body. The signals representing these measurements are then processed in circuits 7 to provide the desired reconstruction of the distribution of attenuation in the examined slice. The processed signals, which now represent attenuation values for elements of the said matrix, are further subjected to display processing in circuits 8 to be provided in a form compatible with a chosen display unit 9. This invention is, however, concerned primarily with the construction of processing circuits 7 and the subject display processing will not be further described.

Circuits 9 require information indicative of the progress of the rotational scan. For this reason the apparatus includes a graticule (shown in part at 10) which co-operates with a photocell unit 11 to provide processing circuits 7 with signals which represent orbital steps $p$.

It has been mentioned that the processing can be based on convolution as described in U.S. Pat. No. 3,924,129 and the disclosure therein is hereby incorporated by reference. In the following description it will be assumed that the signals are arranged in sets and the signals of each set have been modified by subtraction of contributions from other signals of the same set and have been interpolated, or "expanded" to produce a larger number of intermediate signals interposed between successive pairs of the original signals. There are, therefore, in each set a plurality of signals relating to a sufficiently large number of paths distributed in a fan, originating at a focus which may be one position of the radiation source or may be a notional focus defined by the scanning used, as defined in U.S. application Ser. No. 934,311 filed Aug. 17, 1978, and now U.S. Pat. No. 4,178,511 in the names of Godfrey N. Hounsfield and Richard M. Waltham, and assigned to EMI Limited. The focus may also be a single detector looking at a number of source position as is possible with the apparatus described in the above-referenced U.S. application Ser. No. 772,689. The invention is then concerned with the distribution of the signals to storage locations corresponding to matrix elements, a procedure known as "back-projection". It should be mentioned that, if the modification of the signals is carried out in accordance with a so-called convolution function appropriate for parallel beam paths, use with signals for a fan distributed set of beam paths requires additional modification of each signal as it is back projected, in accordance with a function of D, the distance of the respective element from the fan focus. In a preferred procedure the function is proportional to $1/D^2$ and a further modification is required dependent on the cosine of the angle of the beam in the fan from the bisector of the fan. The theory of the modification for fan distributions of the beam paths may be found, inter alia, in said reference "Reconstruction Using Divergent-Ray Shadowgraphs"; the present invention being concerned with a beneficial apparatus for and method of achieving the weighting by the function of D.

Figure 2:
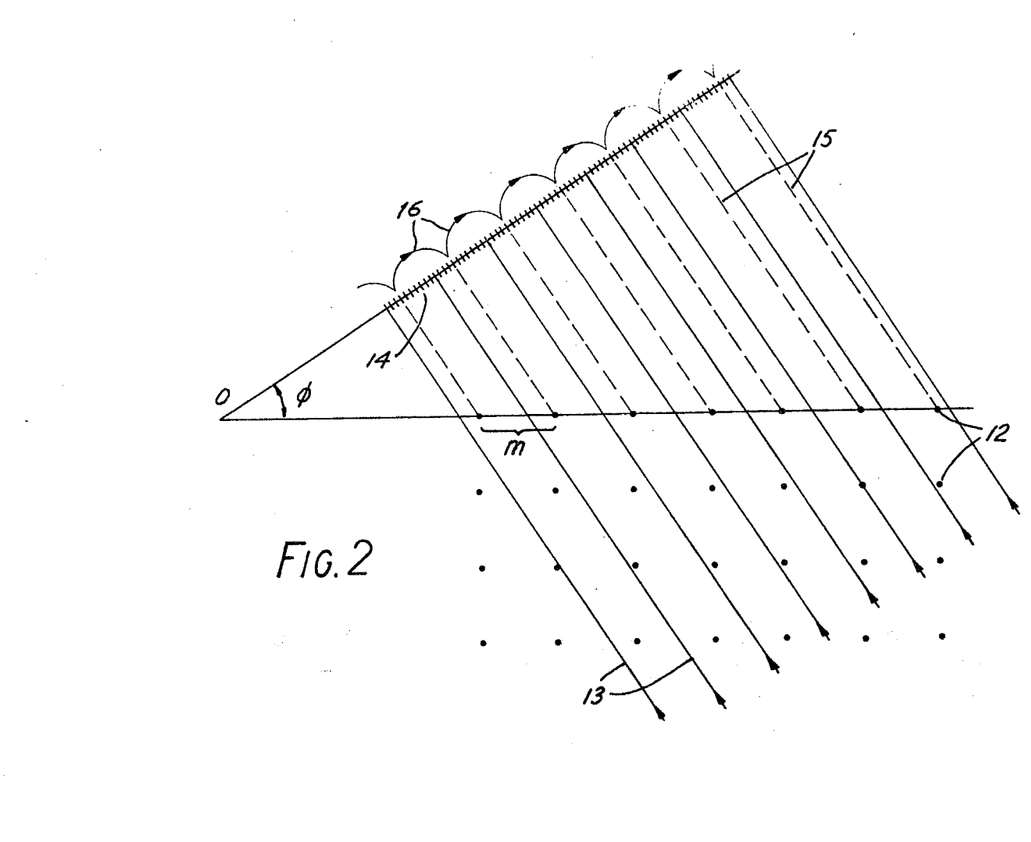
FIG. 2 shows a known method of back-projection of signals relating to parallel beam paths.

One aspect of the processing required for back projection may be more clearly seen from consideration of the simpler case of back projection of signals for parallel beam paths. For the purposes of explanation of this there is shown in FIG. 2 a simplified view of the geometry of that case. In that Figure there can be seen part of the cartesian matrix of elemental areas, in the region of the body 1 being examined; each elemental area is considered to be a solid element with rectangular sides and is denoted by its centre point 12. Each point 12 has a corresponding storage location in a so-called matrix store in which the representation is to be assembled and the signals are to be organised in the store in a manner simulating the procedures to be described.

The matrix elements are spaced at separation m and are intersected by beams of radiation which are indicated at 13 by their centrelines. The beams may be of beam width equal to the distance between their centrelines or may in fact overlap. Sets of beams such as that shown intercept the body at many different orientations for a single examination. The normal to the set shown is inclined at an angle $\phi$ to the matrix rows. The back projection procedure requires that for each storage location there is summed the modified absorption data for all beams, one for each such set, the centre lines of which passes through the corresponding matrix element. If the centre of an element is actually intersected by a beam (as identified by its centreline) for the set shown the modified attenuation signal is applied with full weight. If however, the centre line does not pass through the centre of an elment, the modified attenuation signal is applied with a weight (less than unity) dependent on the distance of the centre line of the beam from the centre of the element. To achieve the desired weighted values, the signals are interpolated to provide intermediate values appropriate to notional interpolated beams having centre lines lying between those of the real ones. A sufficient number of interpolated values are provided to ensure that one notional or real beam passes at least close to the centre of each matrix element. The positions of the centre lines of interpolated beams are shown in FIG. 2 at 14. The interpolation may be effected in conformity with a suitable interpolating function.

The signals could be allocated to the storage locations in any desired order. However it is desirable to adopt a sequence which is efficient in use of signal paths in the electronic circuits used. It is therefore desirable to back-project at one time in to a well defined group of storage locations, which may typically represent a row, column or even a diagonal of the matrix elements. For example each storage location coresponding to the upper row of centre points in FIG. 2 receives, from the set of beams shown, a value for the respective notional beam shown by a broken line 15, which is extrapolated from one of the positions 14.

The set of interpolated (expanded) signals is held temporarily in respective storage locations in a store for the interpolated signals storage in the processing unit 7 (after modification and interpolation) and the back-projection involves stepping through the stored values for a set from an arbitrary point and transferring the signals from the store for the interpolated signals to the matrix store. If the stepping is set to start from an arbitrary origin 0, conveniently the centre of rotation of the scanning means 2 then, after an initial adjustment, the addresses of the matrix store are stepped through by the circuit in equal increments or steps of m units and this will be the same for each matrix row or column. To keep step the interpolated-signal store addresses must step through equal increments 16 of m cos $\phi$. The magnitude cos $\phi$ is the ratio of the distance between the centres of adjacent matrix elements to the distances between the centre lines of the beams represented by the expanded signals. This will change for a different beam path set at a different angle $\phi$ but it is at least constant for one set and need only be recalculated for a change of set. In practice a value of Cos $\phi$ will be provided from a memory in the circuit 7 organised to operate as a look-up table for a value of $\phi$ provided by sensors on the CT equipment. At each step the corresponding signal is transferred from the current address in one store to the current address in the other.

The procedure so far described for parallel sets of beam paths has been used in practice in the CT scanners manufactured and sold by EMI Medical Ltd and EMI Medical Inc. and is well understood. It is, therefore, preferable to use a similar procedure for fan distributed sets of beam paths.

Figure 3:
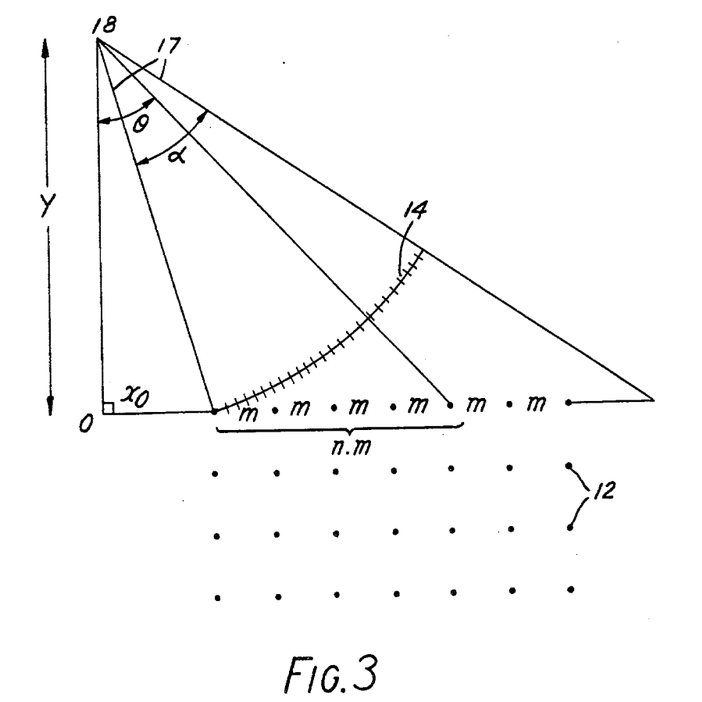
FIG. 3 is used to explain a similar method for sets of beam paths distributed in a fan.

FIG. 3 shows the simplified geometry of the fan arrangement, having the same matrix of elements represented by the centre points 12 intercepted by a fan distribution of beams (not shown individually) extending between limits 17 over an angle $\alpha$ from a focus 18. The expansion process is the same as for parallel sets but now produces a group of modified and interpolated absorption signals equiangularly disposed on an arc about 18 (as represented by 14) to relate to their respective real or notional beams, it being understood that as for the other figures the numbers of absorption measurements and matrix elements are much reduced from typical values, for the sake of clarity.

The procedure for back projecting the signls to the matrix store may be essentially the same as in the parallel set case but, for equal steps of address along the matrix row, the interpolated signal store address is stepped by different increments related to angle $\theta$, which is the angle of an individual fan beam, notional or real, to the matrix columns. It will be seen that on proceeding away fom the origin 0 each successive step in numbers of signal values 14 will be smaller. If the addresses in the store for interpolated or expanded signals are identified by values of $\theta$, which is convenient, then for a matrix element $x_o+nm$ from 0 the correct interpolated value to be selected and applied to the respective storage location in the matrix store can be determined by the equation $\theta=\tan^{-1}[(x_o+nm)/y]$ from 0. This can be determined as before with the aid of a memory organised to operate as a look up table but the arctangent memory must be accessed for each step (since the equation is dependent on n, the number of steps) and this is a time consuming procedure.

In practice the back projection for a row of matrix elements is accomplished under control of a circuit which is repeatedly operated to route the signals appropriately for each different row and each different set of beam paths. A preferred processing method therefore reorganises the interconnections of the processing circuits so that the look-up tables for arc tangent need only be accessed once for the back projection of a set to all the storage locations of the matrix store and not for each storage location.

Figure 4:
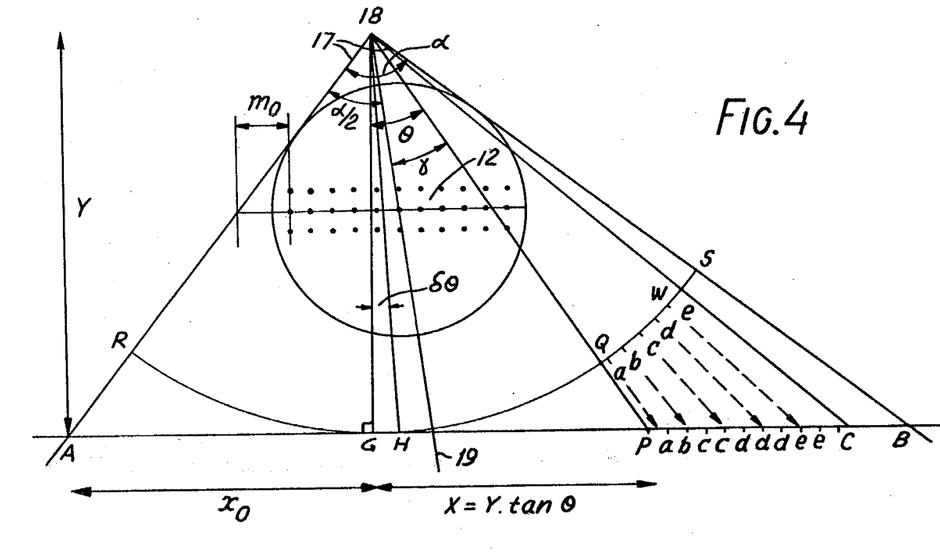
FIG. 4 is used to explain an improved method of distributing signals relating to fan distributions of beam paths.

FIG. 4 shows a radiation fan of angle $\alpha$ disposed about a centre line 19. As in FIG. 3 the modified and interpolated signals can be considered to be for beam paths disposed at equal spacing along arc RGQWS. As mentioned before, in one arrangement this arc can represent a line of detectors on an arc centred on an x-ray source at 18. It is desired to back project the interpolated signals into storage locations corresponding to matrix elements 12, of which three rows are shown. It is proposed to first project the signals onto a line AGHPB, parallel to the matrix rows, and tangential to RGQWS, bearing in mind that the actual procedure involves operating on electrical signals in simulation of the geometrical procedures described. The line AGHPB is at a distance Y from the fan focus or virtual focus 18 and the angle $\theta$ of a beam is defined from the line from focus 18 to point G. Also defined is the angle $\gamma$ which is the angle between the centreline of a beam and the centreline (bisector) 19 of the fan angle $\alpha$. With these definitions, back projection is exactly as explained in relation to FIG. 3, with each successive step along the interpolated value locations on RGHQS requiring access to arctan lookup tables, as GQ=arctan (X/Y). Two further conditions are imposed, however. The first is that all of the interpolated signals for beam paths on RGHQS are projected on to AGHPB along corresponding radii originating at 18, not merely those passing through one row of matrix elements. The second condition is that the loctions to which they are projected are equally spaced along AGHPB although the equiangular lines of projection are not so equally spaced.

The definition used is that for section GH, where the small arc on $\delta\theta$ is close to a straight line, the locations on the line correspond with sufficient accuracy to the equally spaced locations on the arc. They are then extended to A and B at the same spacing. The projection is carried out so that for each location on AGHPB there is selected the interpolated signal corresponding to the beam projected along the nearest equiangular radius. This procedure, shown for a limited number of interpolated values (labelled a to e) between Q and W means that at the extremes of AGHPB several locations receive the same value. For this reason the procedure is called "stretching".

Having projected the interpolated signals onto AGHPB, they are then back projected into the storage location of the matrix store corresponding to the elements of the parallel matrix rows. In this back projection, in conventional manner, only the stretched values for the notional fan beam closest to each matrix element is back projected in each case.

The back projection as before includes stepping the addresses in the matrix store in equal increments along the matrix elements and similarly stepping the corresponding addresses in the store for the "stretched" signals in increments along A to B, transferring the appropriate values. In this case, however, the spacing of matrix elements in any one line corresponds to equal numbers of steps along AGHPB. Although there are different numbers of steps for different matrix rows, the change required is simply in the ratio of the distance of the row along the line from the fan focus 16 to point G.

It will be apparent that the effects of stretching the detector output signals onto AGHPB and then back projecting along matrix rows are that: the arctan lookup tables are accessed only once for each interpolated signal, the steps for each matrix row are of equal value and the steps from one matrix row to the next, for one fan set of beams, are in a simple ratio.

Although FIG. 4 shows only one fan set of beams it should be understood that signals for many such sets of beams are stretched onto the same line AGHPB, which can be called the line of stretch. When the fan centre line exceeds 45° from the perpendicular to the line of stretch, a new line of stretch, 90° displaced, is used and back projection is onto the matrix columns. If desired an intermediate line of stretch may be used to back project into storage locations corresponding to matrix diagonals. The relevant consideration is that, for any sequence of storage location into which the signals are to be back projected, the line of stretch is parallel to that sequence. Although in FIG. 4 it is shown external to the matrix of elements 12, in a preferred embodiment the line of stretch is one such row, column or diagonal, preferably central to the matrix. It should also be mentioned that it is important that the modified values are interpolated or expanded onto arcs such as RGHQS to stretching and not expanded onto the line of stretch.

The method of organising processing circuits, using the concept of the line of stretch, described hereinbefore, is the invention of D. M. Watson and is described and claimed in his U.S. patent application Ser. No. 37,530.

An important feature of the method for convolution processing of fan distributed sets of attenuation signals is the multiplication of each signal, prior to back projection, by an adjustment factor inversely related to D, for the element onto which it is to be projected. In the preferred embodiment the factor is $1/D^2$ but it may be, for example $1/D^3$. The adjustment factor is, in fact, part of the convolution processing and not the back projection and is a consequence of the change in beam path spacing at different distances from the fan focus. Since, however, it is different from different elements of the matrix, where one beam path will intercept several such elements, it is convenient to apply the adjustment during back projection when the positions of the elements are being considered in any case.

In the most straightforward application of the factor each signal being back projected is multiplied by $1/D^2$ immediately before it is back projected from the line of stretch to the respective matrix element or, if the invention of the said co-pending application is not being used, from the arcuate interpolated set to the matrix element. Such a procedure, however, requires this difficult and cumbersome scaling by a variable signal to be performed at each smallest step of the processing.

This invention avoids that necessity by weighting the modified and interpolated data by a factor related to Cos $\theta$, as defined in FIG. 4, prior to back projection of each fan set. This pre-weighting factor, which is $\cos^2 \theta$ for the $1/D^2$ adjustment, is different from the Cos $\gamma$ factor referred to hereinafter and is additional to that Cos $\gamma$ factor where the latter is required. Following that step and during the back projection itself it is merely required to weight the data values for each line of matrix elements being back projected, by a scaling factor which changed from line to line. If the improved back projection of the aforementioned co-pending patent application is being used than the scaling factor is applied to signals as they are derived from storage representing the line of stretch for one row, column or diagonal of the matrix.

This procedure, which avoids the undesirable scaling for each matrix element, is nevertheless chosen to achieve the same effect. This is achieved by a recognition that the procedure can be considered as a particular geometrical arrangement of beams in relation to the patient and suitable consideration of that geometry can allow derivation of a more efficient procedure.

Figure 5:
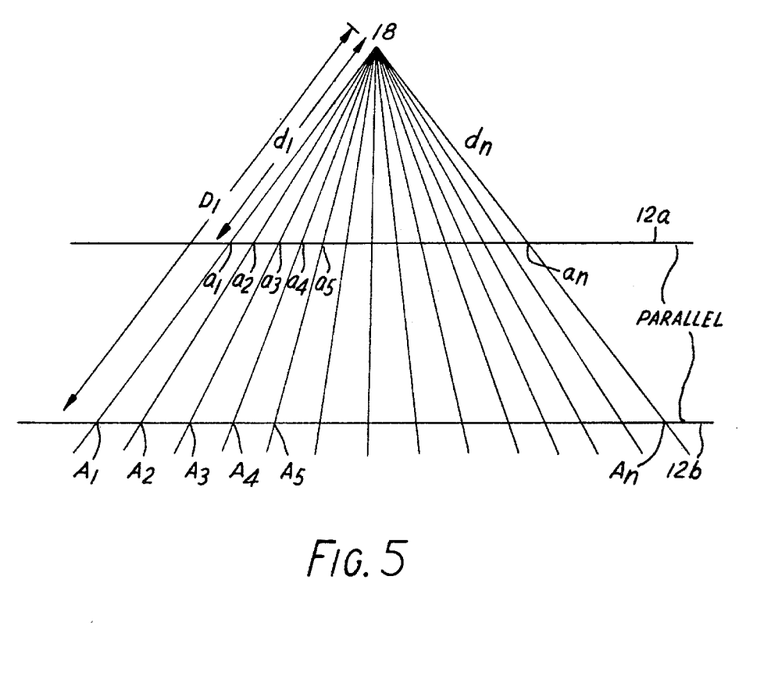
FIG. 5 is used, in conjunction with FIG. 4, to explain the improved arrangement of this invention.

The geometry by which the system is considered is shown in FIG. 5, which shows a plurality of lines, which can be the beam path centrelines, in a fan originating at a point, which can be the fan focus 18. The fan is intercepted by two parallel lines 12a and 12b which may for the moment be considered to be two lines of matrix elements; the elements of the first being $a_1$, $a_2$ etc. and at distances $d_1$, $d_2$ etc. from 18 and these of the second being $A_1$, $A_2$ etc. at distances $D_1$, $D_2$ etc. from 18. Now from the known geometry for parallel lines $D_1/d_1 = D_2/d_2 = D_3/d_3 =$ constant C etc. Considering the description above it will be remembered that the same signal is to be added to the locations for $a_1$ and $A_1$ but the former is to be weighted by $1/d_1^2$ and the and the latter by $1/D_1^2$. However $(D_1/d_1)^2 = $(constant)$^2$. Therefore if the data value has been pre-weighted by $1/D_1^2$ for location $A_1$ it only needs to be weighted by the (constant)$^2$ to be suitable for $a_1$. Furthermore since $D_1/d_1 = $ all $D_n/d_n = $ constant, the same (constant)$^2$ is suitable for all corresponding pairs of elements on lines 12a and 12b.

This can be extended to all other lines of elements parallel to line 12a. Thus part of the procedure of this invention involves weighting the signal for each beam in a fan set by $1/D^2$ of one line 12b and then to make them suitable for any parallel line of elements they are merely scaled by scaling factor $C^2$ where C is the ratio of the distance of the line of elements from focus 18 to the distance of line 12b from focus 18.

It will be understood that line 12b need not itself be a line of matrix elements; it can be any line parallel thereto for which the initial scaling is performed. If the procedure of the said co-pending application is to be followed then line 12b can conveniently be the line of stretch.

Since the chosen line 12b is at a constant particular distance from focus 18 for all matrix elements and one fan set it is now possible to rearrange the initial scaling by $D^2$. Considering the line of stretch AGHPB of FIG. 4, on which the distance from point P to focus 18 is D for the signal corresponding to P, it will be seen that $D = Y/\cos \theta$. Therefore $1/D^2 = \cos^2\theta/Y^2$. Thus, if the signals in the store representing the line of stretch are weighted by $\cos^2\theta$ for their respective angular positions from the perpendicular to G, the $D^2$ scaling is effectively achieved apart from constant $Y^2$. This $Y^2$ factor may be incorporated into the scaling factor discussed before so that the scaling factor becomes K where $K = C^2/Y^2$. Although the weighting by $\cos^2\theta$ has been described for FIG. 4 it is applicable to any line 12b whether it is used as a line of stretch or not.

It should be understood that although the steps to be followed have been described in terms of the system geometry, the desired effect is achieved by following the steps on the electrical signals field in store using predetermined weighting factors.

FIGS. 2, 3 and 4 represent simplified explanations of one possible view of the operation of the electrical and electronic circuits implementing this invention.

Figure 6A:
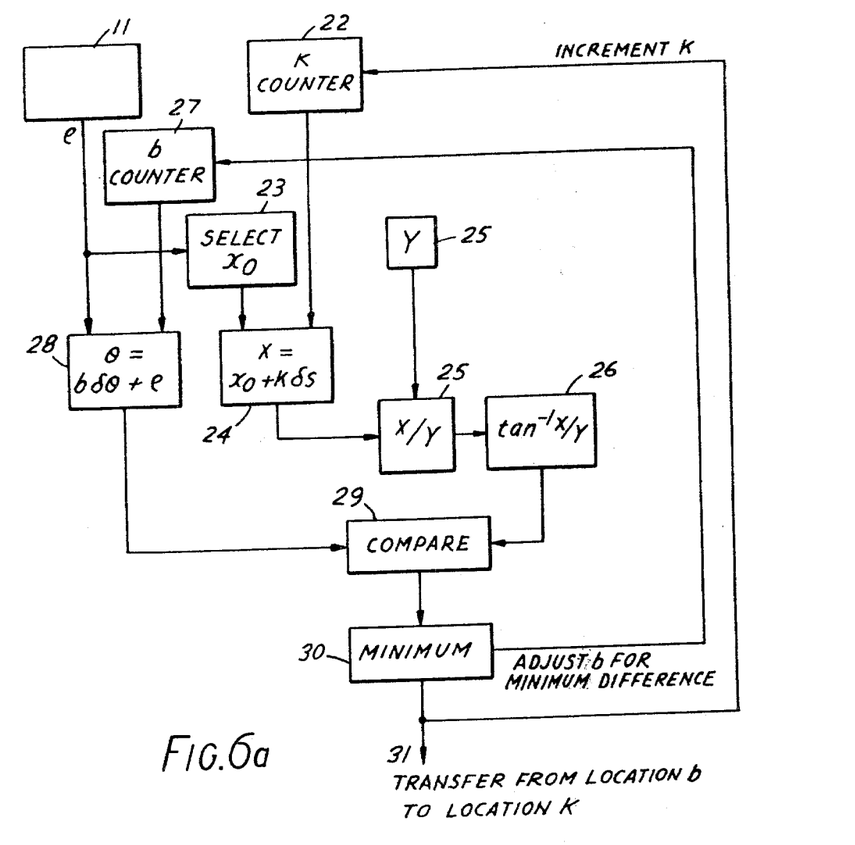
FIGS. 6a and 6b are block diagrammatic circuits of one embodiment of part of the FIG. 1 apparatus.
Figure 6B:
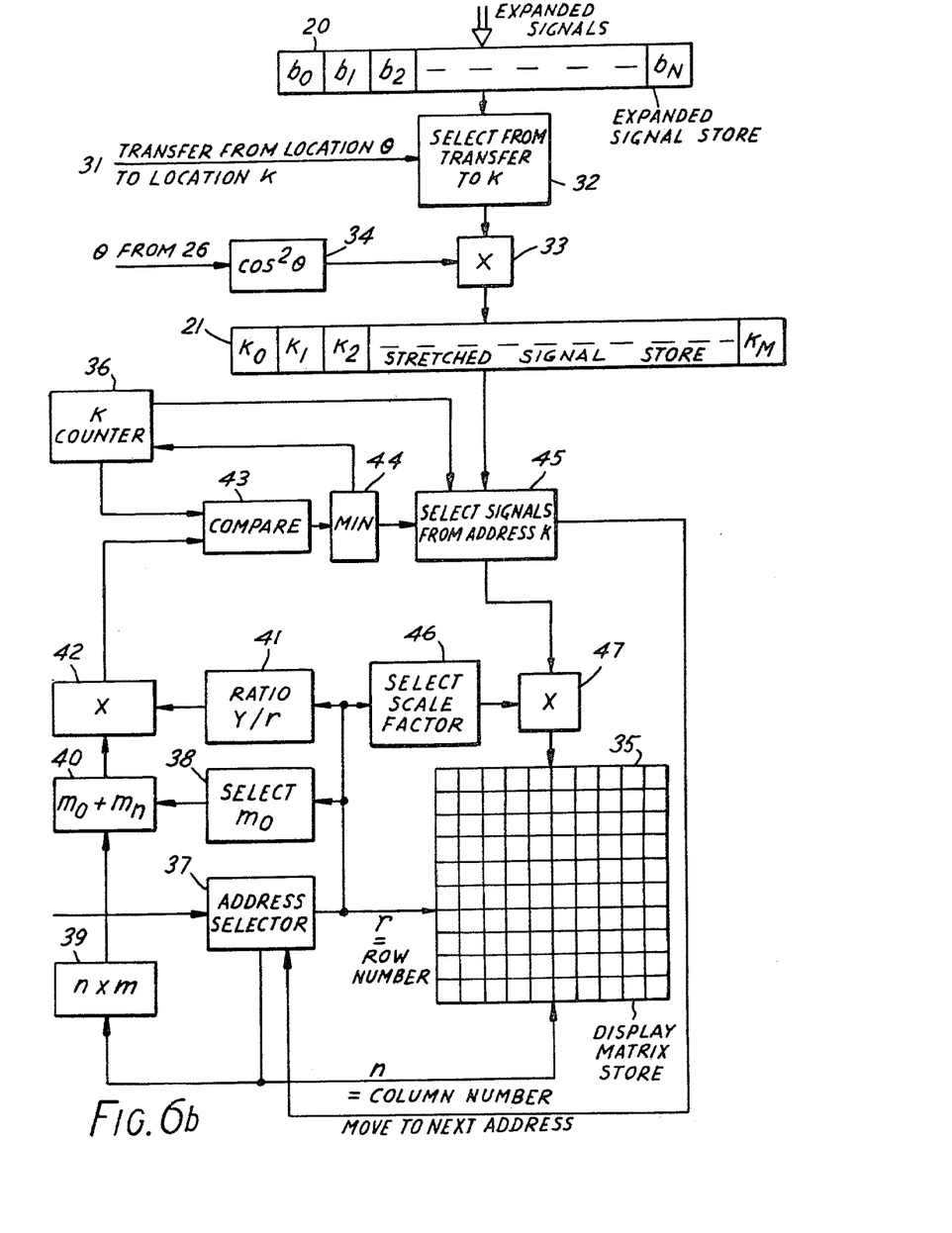

In FIGS. 6a and 6b which will be explained with reference to FIG. 4 there is shown an actual embodiment of the invention. This circuit will be explained for operation on X-ray signals for a sequence of fan sets of beam paths within the required angle of one line of stretch. It will be understood that the sequence is restarted with a new line of stretch when $\theta$ exceeds a suitable value. Successive sets of signals correspond to adjacent fan sets of beam paths whose median lines 19 are spaced at angular increments $\rho$. A value of $\rho$ for each set is provided by the photocell unit which indicates the current scan position.

The expanded values are considered to be for beam paths, along line RGHQS starting at R and are in fact held in a store 20. Each value corresponds to a value of $\theta$, which is the inclination of the respective beam to the perpendicular to the line of stretch. Thus the FIG. 4 arrangement values of $\theta$ between R&G will be negative. However $\theta$ is defined in the circuit as $b\delta\theta + \rho$ where $\delta\theta$ is the step between adjacent beam paths and b has the value 0 at R and N at S. Each signal in store 20 can thus be labelled with its b value as $b_0, b_1 \ldots b_N$.

The signals are to be stretched onto line of stretch AGHPB by being entered into store 21 at locations corresponding to positions, on the line of stretch, spaced at $\delta s$. Each position is at a distance X from point G where $X = x_0 + k\delta s$ so that X is stepped in response to the stepping of integer k from 0 to M. Similarly the signals are in locations labelled $k_0$ to $k_M$.

The arrangement is such that k is stepped regularly from A to B and b is stepped from 0 to N in response to the changes in k. The signal in the location of the current b value in 20 is transferred to the location in 21 having the current k value.

As explained before some expanded signals are used more than once as stretched signals and therefore b is not stepped each time k is stepped.

FIG. 6a shows a circuit for deriving control signals which control the transfer of detector output signals after interpolation or "expansion". Counter 22 holds the current value of k. For each set of signals there is a predetermined $x_0$ which is supplied by a store 23 in response to the $\rho$ input from 11, identifying the set. Combining inputs from 22 and 23, unit 24 determines the current value of $X = x_0 = k\delta s$. This is supplied together with the value of Y, which preset for the equipment is held in read only memory 25, to divider 26 which provides X/Y. Unit 26, organised as a look-up table provides $\tan^{-1} X/Y$ from the X/Y input. This gives in effect the angle of the notional beam path going through the current stretched point. The current b value is held in a counter 27 and a unit 28 takes the values of b and $\rho$ and provides the corresponding $\theta$ from $\theta = b\delta\theta + \rho$. Unit 29 compares this with $\tan^{-1} X/Y$ and gives the result to unit 30. Unit 30 detects a minimum on the output 29 and instructs counter 27 to change the value of b until it is achieved. Such arrangements are well known. When the minimum is achieved the corresponding values of b and k are provided at 31.

Turning now to FIG. 6b which shows the circuits which actually handle the detector output signals, the b and k values are provided to address selector 32 which effects the transfer from corresponding locations in store 20 to store 21. At this stage the signals are weighted by the required $\cos^2\theta$ factor in a multiplier 33. The current value of $\theta$ is given by $\tan^{-1} X/Y$ from 26 and converted to $\cos^2\theta$ in a store 34 which is organised as a look-up table.

The next stage is to project the signals onto locations, in a matrix store 35, which correspond to matrix elements. There are, of course, many more locations than indicated in FIG. 6b. The transfer is essentially the same as that just described for stores 20 and 21 except that store 35 is two-dimensional, that is to say it includes storage locations corresponding to each element of the Cartesian matrix notionally delineated in the region of interest. A further counter 36 steps through k as before (but independently of and subsequent to 22). The problem is then to achieve a value of k for each matrix element location corresponding to a stretched signal for a beam path therethrough. An address selector 37 selects a matrix location in store 35 identified by a row number r and a column number n; the selector 37 is preset to increment along a row and then to return to the start of the next row. From FIG. 4 it will be seen that each row has a different value of $m_o$ (the distance of the first location to the beam from 18 through R and A). A store 38 provides the value of $m_o$ from each r. As described hereinbefore the matrix elements are spaced by distance m so that each element is identified by $m_o + mn$. A multiplier 39 provides $n \times m$ from the n input and adder 40 provides $m_o + mn$. In fact the matrix elements are at constant spacing but the beam paths are divergent. Thus to relate to the stretch points k an expansion factor, the ratio of distance Y to row number r (which is effectively the mean radius from 18), is required. This is provided by divider 41 and multiplier 42 multiplies the output of 40 by this factor.

The output of 42 is the quantity indicative of the real or notional beam through the matrix element which can be compared with k to identify the correct location in store 21. As before they are compared, in a comparator 43, and a minimum detector 44 increments k to the required value. When the correct k value has been found address selector 45 locates the corresponding data value in store 21 and applies it to 35. Selector 45 also instructs address selector 37 to change to a new matrix location.

As each stretched signal is applied to the matrix store 35 it needs to be weighted by the scale factor for the respective row. The scale factor can be precalculated for the matrix to be reconstructed and the X-ray apparatus used and the factors stored in store 36. Multiplier 47 then applies the selected factor to the signals.

It is emphasized that the foregoing description has assumed that projection is only onto matrix rows. As projection will normally also be onto columns, and perhaps diagonals, consequential modifications will need to be made to the address selectors to permit the required rotation. The procedures required are straightforward to those with appropriate skills.

Figure 7:
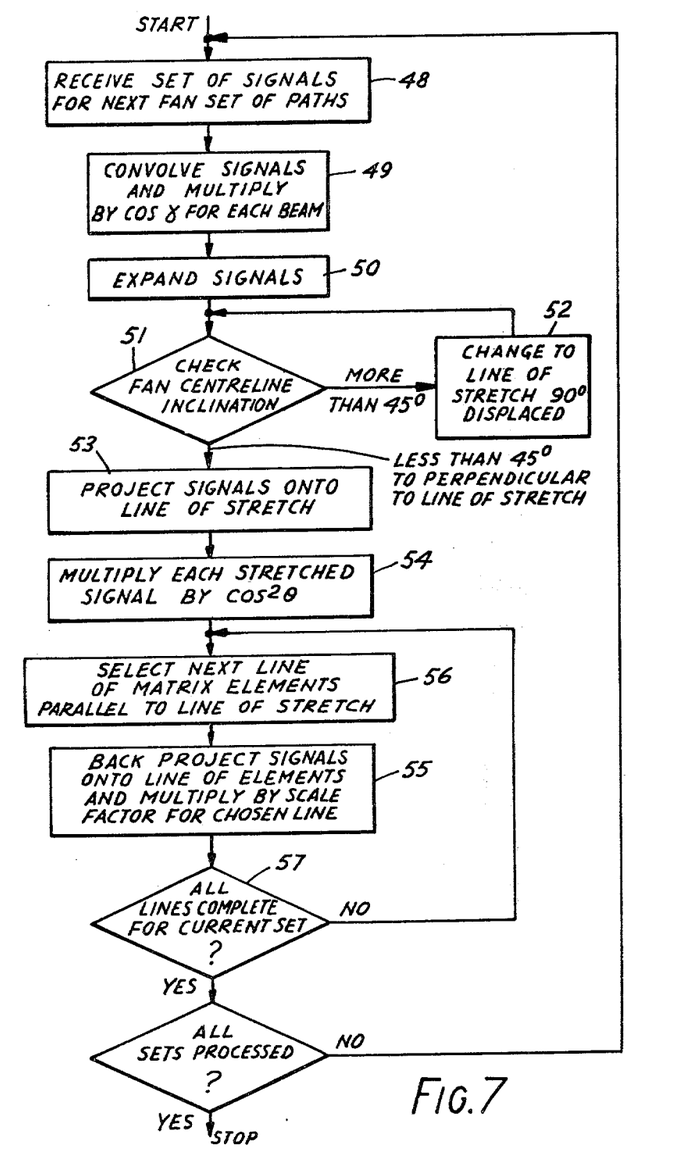
FIG. 7 is a flow diagram showing the sequence of back-projection used in this invention.

It has been stated hereinbefore that the block 7 in FIG. 1 provides processing steps which include the back projection described. The exact nature of these circuits, to achieve the procedure described, is not limited to one particular form but can be varied to suit the processing equipment available. The important consideration for this invention is that the weighting by $\cos^2\theta$ and subsequent weighting by the relevant scaling factor should be carried out at the correct stages of the processing to give a suitable improvement in efficiency. To further assist understanding of the processing to take place in block 7, a flow diagram showing the sequence of operation is shown in FIG. 7.

The processing described in relation to FIG. 5 is performed on each set of signals in turn, recycling until all of the sets for one examination have been processed. Each set of X-ray detector output signals received (48) is convolved with the chosen convolution series in the manner described in U.S. Pat. No. 3924129 making due allowance for the fan distribution of paths to provide modified signals (49). During this procedure each value is also weighted by $\cos \gamma$, where $\gamma$ is the angle in the set of the respective beam path from the centreline of the fan. This is in accordance with the preferred convolution method for fan sets and may not be required for other methods.

The data are next expanded (50) to provide sufficient values along the arc (such as RGHQS). This is achieved by interpolation which can conveniently be the third difference interpolation described in U.S. Pat. No. 4,002,910. If the mean angle of the fan set is near enough to the perpendicular to the chosen line of stretch (51) then the next stage is followed. If the deviation is excessive then the line of stretch is rotated through 90° (52) to be more suitable for the fan being processed. Having provided a suitable line of stretch, the modified and expanded signals are projected onto the line using the arc tangent relation explained hereinbefore and arc tangent look up tables (53). The stretching is performed so that the modified and expanded signals are distributed uniformly along the line of stretch at a spacing approximately the same as the original spacing along the arc. Some signals are used more than once on the line of stretch as required to achieve that spacing.

As the first stage of the procedure to achieve, in effect, the scaling by $D^2$, the signals distributed along the line of stetch are weighted by $\cos^2\theta$ (54). In this case $\theta$ for each value is the angle in the fan of the path, real or notional, joining the position of the value of the line of stretch with fan focus 18. Values for $\theta$, originally provided by the CT apparatus for real beam paths, are generated for notional paths on the processes of expansion and stretching.

When this preweighting has been effected, the signals are back projected (55) onto those matrix elements lying along their respective real or notional paths. During back projection the second stage of the effective $D^2$ division is carried out. Each signal which is back projected is weighted at the same time by the scale factor for the relevant line of elements. The scale factors can be worked out as required for each line since, as can been seen from the description herein, the considerations are relatively straightforward. It will be understood, however that the processing carried out for one examination can be identical, except for the absorption signals themselves and certain routine calibrations and corrections, with that for other examinations. In that case it is convenient to determine the scale factors and other processing factors in advance by consideration of the geometry of the system. They can then be held in store to be derived and used as required. As mentioned hereinbefore, the back projection is, in the embodiment, performed for elements in lines parallel to the line of stretch. Adjacent lines of elements are dealt with in sequence (56) until all lines of elements have been dealt with for the current fan set of paths (57). In this example the lines of matrix elements are rows or columns since the line of stretch rotates through steps of 90° as required. However it can be rotated through 45°, say; every second rotation then causing back projection onto diagonal lines of elements.

When all of the fan sets of absorption data have been processed in this way, the procedure is terminated and the representation which has been assembled is available for further processing and display.

Although the invention has been described primarily in terms of the circuits shown in FIGS. 6a and 6b, it will be appreciated that the preferred circuits can be realised by a digital computer dedicated, by a suitable program and by appropriate interconnection to other parts of the apparatus, to the described tasks. In that event the flow diagram of FIG. 7 will provide guidance for the required programming.

What I claim is:

1. An apparatus for processing signals derived from a computerized tomographic scanner and relating to attenuation suffered by x-radiation on traversing each of many substantially linear paths across a cross sectional slice of a body under examination, said scanner supplying the signals in groups relating to sets of paths, the paths of each set diverging from a focus and the focus for each set being disposed at a different angular location relative to the cross-sectional slice and the signals in each group being supplemented as required by signals, formed by interpolation between the first mentioned signals, to represent attenuation for divergent paths not actually irradiated, the processing apparatus including: a matrix store having a plurality of locations each of which is allocated to one of a plurality of elemental regions of the body, said elemental regions being disposed in a rectangular array in said slice; means for selecting and distributing to the locations of the matrix store contributions from the signals, both measured and interpolated, relating to paths traversing the corresponding elemental regions of the body; means operative prior to the selection and distribution of the said contributions for weighting each contribution from the signals of a group by a factor related to $\cos\theta$ raised to a selected power, where $\theta$ is the angle between the path corresponding to the signal from which the contribution was derived and the perpendicular to a plurality of parallel lines of the elemental regions; and scaling means arranged to scale the contributions being distributed to storage locations corresponding to one of said parallel lines by a scaling factor chosen for that line such that the contributions distributed to each location for the line have, after weighting by said factor related to $\cos\theta$ and the scaling factor, been weighted by $1/D$ raised to the same power as $\cos\theta$, where D is the distance between the elemental region corresponding to the location, and the focus for the respective group.

2. An apparatus according to claim 1 wherein the means for weighting is arranged to multiply each of the contributions by $\cos^2\theta$.

3. An apparatus according to claim 1 wherein the means for weighting is arranged to weight each of the contributions by $\cos\theta$.

4. An apparatus according to any one of claims 1, 2 or 3 in which the scaling means is arranged to scale the contribution by a scaling factor which is the same power of a constant proportional to the perpendicular distance of the respective line to the said focus as the power to which $\cos\theta$ is raised.

5. An x-ray machine comprising:
   means for irradiating a region with x-rays and for deriving signals related to the manner in which the region attenuates the x-rays;
   means for converting the signals to modified signals which are in groups arranged such that the modified signals of each group are related to directions which fan through the region and have a common focus, and each modified signal within a group is related to a respective one of the directions within the fan, there being a multiplicity of such fans having respective foci distributed around the region;
   signal storage locations for accumulating respective picture element signals for the respective elements of a rectangular array of elements of the region;
   means for weighting said modified signals by respective weighting factors, wherein the weighting factor for a given modified signal is related to the cosine, raised to a selected power, of the angle between (i) the respective direction related to the modified signal and (ii) the perpendicular to a number of lines which are parallel to each other and each of which passes through a respective set of region elements; and means for using the so weighted modified signals to accumulate and build up an electronic picture of the region in said signal storage locations and for displacing said picture;

said means for using the weighted modified signals and displaying the picture including means for causing the signal storage locations to accumulate contributions from said weighted modified signals such that the contributions to the signal storage locations for one of said sets of region elements from one group of weighted modified signals are determined by scaling each of the signals of the last recited group by the same scaling factor.

6. An x-ray machine as in claim 5 wherein the means for using the weighted modified signals and displaying the picture of the region includes means for causing said same scaling factor for said one set of region elements to be related to the distance between the focus of the respective fan and the set of region elements.

7. An x-ray machine as in claim 6 in which said means for using the weighted modified signals and displaying the picture of the region includes means for causing said same scaling factor to be related to said distance raised to the same power as said cosine of said angle.

8. A method of taking an x-ray picture of a region comprising the following steps each of which is machine implemented:

irradiating a region with x-rays and deriving signals related to the manner in which the region attenuates the x-rays;

converting the signals to modified signals which are in groups arranged such that the modified signals of each group are related to directions which fan through the region and have a common focus, and each modified signal within a group is related to a respective one of the directions within the fan, there being a multiplicity of such fans having respective foci distributed around the region;

providing signal storage locations for accumulating respective picture element signals for the respective elements of a rectangular array of elements of the region;

weighting the modified signals by respective weighting factors, wherein the weighting factor for a given modified signal is related to the cosine, raised to a selected power, of the angle between (i) the respective direction related to the modified signal and (ii) the perpendicular to a number of lines which are parallel to each other and each of which passes through a respective set of region elements;

using the so weighted modified signals to accumulate an electronic picture of the region, said using step including the substeps of causing the signal storage locations to accumulate contributions from said weighted modified signals such that the contributions to the signal storage locations for one of said sets of region elements from one group of weighted modified signals are determined by scaling each of the signals of the last recited group by the same scaling factor; and displaying said picture of the region.

* * * * *

UNITED STATES PATENT AND TRADEMARK OFFICE
CERTIFICATE OF CORRECTION

PATENT NO. : 4,275,444
DATED : June 23, 1981
INVENTOR(S) : John L. Ryan

It is certified that error appears in the above-identified patent and that said Letters Patent are hereby corrected as shown below:

Abstract, line 5, delete "It" and insert -- If --.

Column 3, line 12, delete "subject" and insert -- subsequent --.

Column 3, line 39, delete "position" and insert -- positions --.

Column 5, line 27, delete "signls" and insert -- signals --.

Column 6, line 17, delete "loctions" and insert -- locations --.

Column 7, line 8, after "RGHQS" and before "to" insert -- prior --.

Column 8, line 7, after "$1/d_1^2$" and before "and" delete "and the".

Signed and Sealed this

Second Day of March 1982

[SEAL]

Attest:

GERALD J. MOSSINGHOFF

Attesting Officer    Commissioner of Patents and Trademarks